(12) United States Patent
Saimovici

(10) Patent No.: US 10,052,227 B2
(45) Date of Patent: Aug. 21, 2018

(54) CATARACT REMOVAL DEVICE AND INTEGRATED TIP

(71) Applicant: Liviu B. Saimovici, Rye, NY (US)

(72) Inventor: Liviu B. Saimovici, Rye, NY (US)

(73) Assignee: Liviu B. Saimovici, Rye, NY (US)

( * ) Notice: Subject to any disclaimer, the term of this patent is extended or adjusted under 35 U.S.C. 154(b) by 920 days.

(21) Appl. No.: 14/029,375

(22) Filed: Sep. 17, 2013

(65) Prior Publication Data

US 2014/0081151 A1 Mar. 20, 2014

Related U.S. Application Data

(60) Provisional application No. 61/714,556, filed on Oct. 16, 2012, provisional application No. 61/702,498, filed on Sep. 18, 2012.

(51) Int. Cl.
| | |
|---|---|
| *A61F 9/00* | (2006.01) |
| *A61F 9/007* | (2006.01) |
| *A61B 5/00* | (2006.01) |
| *A61B 1/00* | (2006.01) |
| *A61B 1/015* | (2006.01) |
| *A61B 1/06* | (2006.01) |
| *A61B 90/30* | (2016.01) |
| *A61B 90/00* | (2016.01) |
| *A61M 1/00* | (2006.01) |
| *A61B 17/32* | (2006.01) |

(52) U.S. Cl.
CPC ...... *A61F 9/00745* (2013.01); *A61B 1/00087* (2013.01); *A61B 1/00094* (2013.01); *A61B 1/00165* (2013.01); *A61B 1/015* (2013.01); *A61B 1/06* (2013.01); *A61B 5/0084* (2013.01); *A61B 5/4836* (2013.01); *A61B 90/30* (2016.02); *A61B 90/361* (2016.02); *A61F 9/00736* (2013.01); *A61B 2017/320004* (2013.01); *A61B 2017/320072* (2013.01); *A61M 1/00* (2013.01); *A61M 1/0064* (2013.01)

(58) Field of Classification Search
CPC .......... A61F 9/00745; A61F 2009/0087; A61F 2009/00887; A61F 9/00736; A61M 2210/0612; H04N 5/23248; H04N 3/1562; H04N 3/1568; H04N 5/23264; H04N 5/2327; H04N 5/23274; H04N 5/23277

See application file for complete search history.

(56) References Cited

U.S. PATENT DOCUMENTS

| 693,358 A | * | 2/1902 | Westlake | ......................... 604/39 |
| 4,531,943 A | * | 7/1985 | Van Tassel et al. | .......... 604/523 |

(Continued)

OTHER PUBLICATIONS

Machekhin V.A. et al. Tekhnika fakoemulsifikatsii katarakty s plotnymi yadrami. Byulleten SO RAMN, 2009, .No. 4, (138), pp. 26-29.

(Continued)

*Primary Examiner* — Scott Medway
(74) *Attorney, Agent, or Firm* — Leason Ellis LLP

(57) ABSTRACT

The present invention is directed to an apparatus and method for assisted removal of the cortex, capsule polishing and destruction and/or removal of other intraocular structures. More particularly, the present invention is directed to a surgical apparatus configurable for removal of the cortex and the polishing of the capsule during cataract extraction surgery.

21 Claims, 16 Drawing Sheets

(56) References Cited

U.S. PATENT DOCUMENTS

| | | | |
|---|---|---|---|
| 4,672,965 A * | 6/1987 | Baum | 606/169 |
| 4,825,865 A * | 5/1989 | Zelman | A61F 9/00736 |
| | | | 604/266 |
| 4,869,715 A * | 9/1989 | Sherburne | 604/22 |
| 5,057,098 A * | 10/1991 | Zelman | A61F 9/00745 |
| | | | 604/22 |
| 5,213,569 A * | 5/1993 | Davis | 604/22 |
| 5,478,338 A * | 12/1995 | Reynard | 606/15 |
| 5,569,279 A * | 10/1996 | Rainin | 606/166 |
| 5,651,783 A * | 7/1997 | Reynard | 606/4 |
| 5,746,713 A * | 5/1998 | Hood et al. | 604/22 |
| 5,755,700 A * | 5/1998 | Kritzinger et al. | 604/257 |
| 5,814,010 A * | 9/1998 | Ziegler | 604/22 |
| 6,007,555 A * | 12/1999 | Devine | 606/169 |
| 6,083,192 A * | 7/2000 | Bath | 604/22 |
| 6,283,974 B1 * | 9/2001 | Alexander | 606/107 |
| 6,319,220 B1 * | 11/2001 | Bylsma | 604/22 |
| 6,425,905 B1 * | 7/2002 | Guimaraes et al. | 606/166 |
| 6,428,508 B1 * | 8/2002 | Ross | 604/118 |
| 6,491,670 B1 * | 12/2002 | Toth et al. | 604/264 |
| 6,544,254 B1 * | 4/2003 | Bath | 606/6 |
| 6,575,989 B1 * | 6/2003 | Scheller et al. | 606/161 |
| 7,037,296 B2 * | 5/2006 | Kadziauskas et al. | 604/294 |
| D556,322 S * | 11/2007 | Akahoshi | D24/144 |
| 8,398,578 B1 * | 3/2013 | Zolli | 604/19 |
| 8,435,248 B2 * | 5/2013 | Herman | 606/107 |
| 8,992,459 B2 * | 3/2015 | Nallakrishnan | 604/22 |
| 2004/0199192 A1 * | 10/2004 | Akahoshi | 606/169 |
| 2005/0234473 A1 * | 10/2005 | Zacharias | 606/107 |
| 2006/0149301 A1 * | 7/2006 | Claus | 606/169 |
| 2007/0002159 A1 * | 1/2007 | Olsen et al. | 348/335 |
| 2008/0294087 A1 * | 11/2008 | Steen et al. | 604/22 |
| 2011/0208114 A1 * | 8/2011 | Morlet | A61F 9/00745 |
| | | | 604/22 |
| 2013/0231605 A1 * | 9/2013 | Walter | 604/22 |
| 2015/0335482 A1 * | 11/2015 | Akahoshi | A61F 9/00745 |
| | | | 604/22 |

OTHER PUBLICATIONS

Shah S.K. et al. "Impact of anterior capsule polishing on anterior capsule opacification after cataract surgery: a randomized clinical trial" Eye (Lond), Aug. 2009; 23(8):pp. 1702-1706 (abstract) [online] [retrieved on Jan. 14, 2014] Retrieved from PubMed, PMID: 19079142.

* cited by examiner

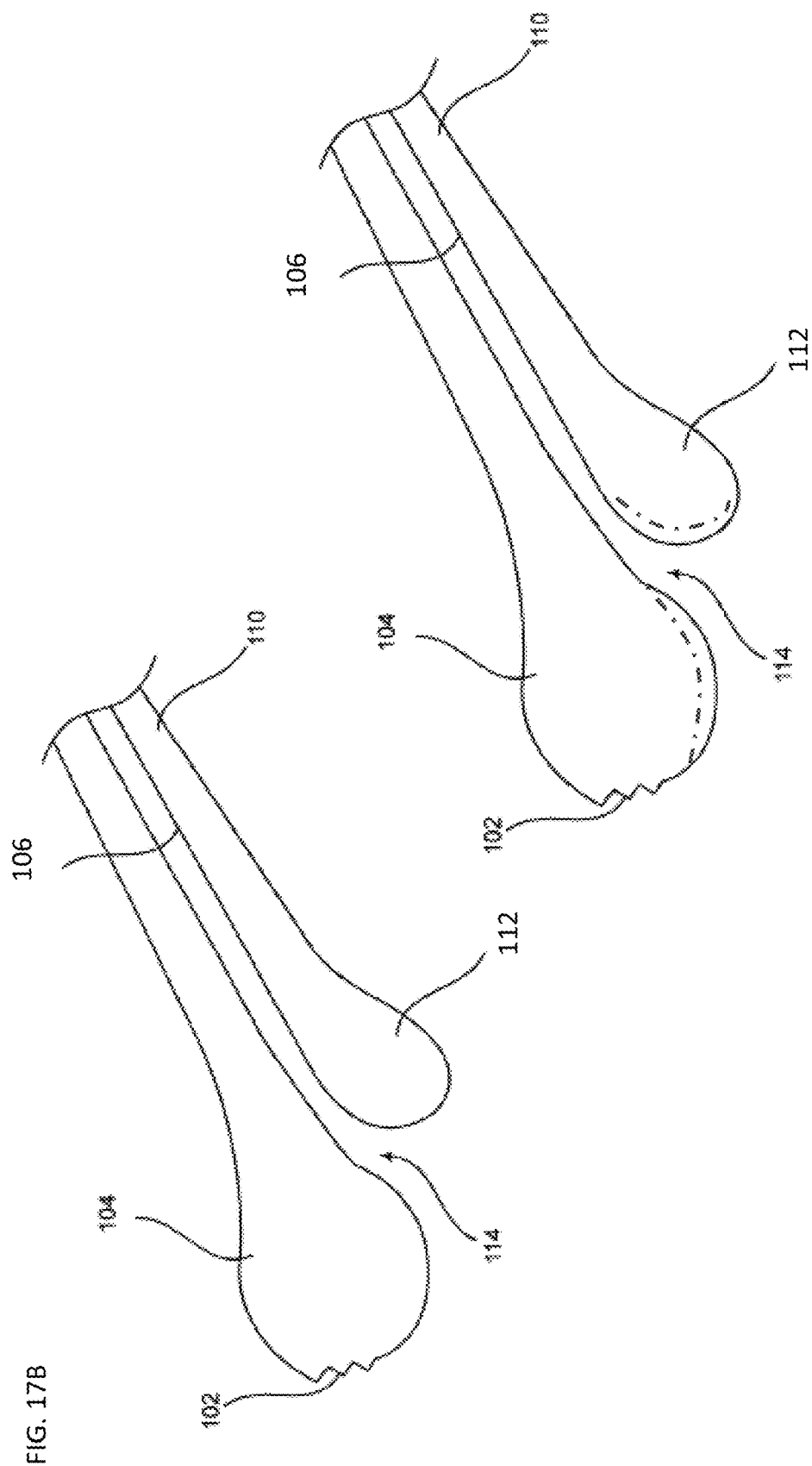

ved by reference in their entireties.
CATARACT REMOVAL DEVICE AND INTEGRATED TIP

CROSS-REFERENCE TO RELATED APPLICATIONS

This application claims the benefit of priority under 35 U.S.C. Section 119(e) of U.S. Application Ser. No. 61/714,556, filed Oct. 16, 2012 and U.S. Application Ser. No. 61/702,498, filed Sep. 18, 2012, which are hereby incorporated by reference in their entireties.

FIELD OF THE INVENTION

The present invention is directed to an apparatus and method for assisted removal of the cortex, capsule polishing and destruction and/or removal of other intraocular structures.

More particularly, the present invention is directed to a surgical instrument configurable for the removal of the cortex, the polishing of the capsule during cataract removal and intraocular lens implantation.

BACKGROUND OF THE INVENTION

The human eye in its simplest terms functions to provide vision by transmitting light through a clear outer portion called the cornea, and focusing the image by way of the lens onto the retina. When age or disease cause the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an intraocular lens ("IOL"). The natural lens or crystalline lens of the eye can be described as having a central part, i.e., the nucleus, surrounded by the cortex, which is in turn surrounded by the lens capsule having anterior and posterior portions.

In the United States, and in most parts of the world the majority of cataractous lenses are removed by a surgical technique called phacoemulsification. During this procedure, a thin phacoemulsification cutting tip is inserted into the diseased lens and vibrated ultrasonically. A typical ultrasonic surgical instrument suitable for ophthalmic procedures consists of an ultrasonic handpiece, an attached cutting tip, an irrigating sleeve and a control console. The handpiece assembly is attached to the control console by an electric cable and flexible tubing. Through the electric cable, the console varies the power level transmitted by the handpiece to the attached cutting tip and the flexible tubing supplies irrigation fluid to and draws fluid and lens material from the eye through the handpiece assembly.

The "phaco" probe is an ultrasonic handpiece with a hollow metal tip. The tip of the phaco probe vibrates at an ultrasonic frequency to sculpt and emulsify the nucleus while a pump aspirates particles of the cataract through the tip. Typically the tip is made of titanium or steel. The tip vibrates at an ultrasonic frequency of about 40,000 Hz. This causes the lens material to be emulsified, such as is described in U.S. Pat. No. 6,319,220 to Bylsma, herein incorporated by reference in its entirety. The aspiration line connected to the handpiece provides aspiration or "flow" that draws the fluid and lens particles into the tip via the pump (e.g. a peristaltic pump, venturi, vacuum pump, etc., or combinations thereof), and overcomes the repulsive force to some extent of the oscillation energy.

After phacoemulsification of the nucleus, but prior to the insertion of a new lens, it is necessary to remove the cortex. Cortex removal is typically accomplished with strictly mechanical means, such as through suction. However, such suction can, and occasionally will, damage the delicate tissues (i.e. capsule and iris) found in the ocular cavity. Contemporaneously, an irrigation instrument is necessary to replace fluid that is extracted during the suction process. Specifically, the fluid pressure of the eye must be maintained during the aspiration procedure or the eye structure will collapse, leading to severe complications. The current art provides a combined aspirator/irrigator tool that incorporates a metal tube closed and rounded at one end but with a side port/hole through which the cortex is aspirated. A second, larger tube/cylinder covers this aspirating instrument. The larger, enveloping instrument is a sleeve that allows for the introduction of a solution into the eye so as to balance the pressure lost caused by aspiration. Thus the procedure includes an irrigation step and an aspiration step. Furthermore, this procedure can be done bi-manually with a properly designed arrangement of instruments.

What is needed in the art is a method and apparatus for the assisted removal of the cortex, capsule polishing and destruction and removal of other intraocular structures, but which reduces the chance of lasting damage to the eye and allows for quicker removal of the cortex.

Furthermore, polishing the capsule (either the anterior capsule or the posterior capsule) is necessary to remove any remaining epithelial cells so as to prevent the generation of a secondary cataract. The capsule is polished to remove the strata (or very fine cortex or layer of epithelial cells) that remain attached to the capsule. The polishing is different from cortex removal since it is directed to removal of a layer of epithelial cells that remain firmly and solidly attached to the posterior surface of the anterior capsule and the anterior surface of the posterior capsule. Specifically, the posterior surface of the remaining anterior capsule and the anterior surface of the posterior capsule need to be polished to effectuate a completely successful procedure. A successful operation requires that the capsule surface be clear of cells and cortex. If the capsule is not completely cleaned and polished of cells, complications will develop.

The procedures described in the art are suitable for the removal of cataracts. However, the procedures described in the prior art carry risks of severe complications such as the risk of infection and damage to the delicate tissues of the eye. In severe cases, the apparatus and methods currently employed, when used improperly or when the tissues and organs of the eye are already weakened, will result in the loss of vision or the eye. Therefore, what is needed is a method and apparatus that allow for the removal of the elements of the cataractous material in a safe and consistent manner.

Additionally, what is needed is an instrument and method directed to the polishing of the capsule that reduces the potential damage to the capsule and the greater optical organ. Furthermore, what is needed is an instrument and method that lower the risk of complications throughout the surgical procedure.

SUMMARY OF THE PRESENT INVENTION

In accordance with a broad aspect of the present invention, the apparatus and method disclosed herein provide for a configuration selectable instrument that allows one of ordinary skill in the art to remove the cortex and polish the capsule using an oscillating instrument. Furthermore, the present invention is directed to a method of removing the cortex and polishing the capsule that provides for a faster, safer, easier, and more consistent cataract operation.

In one example of the described invention, an instrument is equipped with an endpiece that combines the features of cortex removal and capsule polishing. In the envisioned configuration, the single instrument is rotatable such that a cortex removing portion is primarily engaged or a capsule polishing portion is engaged depending on the orientation of the instrument. In one exemplary embodiment of the envisioned instrument, a top side of the instrument (by "top side" a person of ordinary skill in the art would understand that this would be the first side of the instrument to come in contact with elements of the cortex, in need of addressing) is used for emulsifying or otherwise degrading the cortex. Likewise, by changing the orientation of the instrument, a trained professional is able to cause the opposing surface of the instrument to engage and gently abrade the posterior surface of the anterior capsule and the anterior surface of the posterior capsule to remove any remaining cortex and epithelial cells. In this configuration, the described instrument is equipped with different surface textures to correspond to the given task. It is envisioned that the instrument or endpiece is vibrated and/or rotated through the use of ultrasonic transducers or other mechanical vibration.

In one particular arrangement, the envisioned method is also directed to removing the cortex and polishing the capsule through the use of an ultrasonically, or otherwise oscillated instrument having a combined cortex removal function and a capsule polishing function. Likewise, the envisioned method involves a series of steps using the instrument described to either remove or degrade intraocular structures.

For example, the proposed method includes the steps of inserting the instrument into the eye cavity and activating the ultrasonic transducers. During the next step, the cortex is removed by degrading the material with one side, surface, or tip of the instrument. For example, the cortex material is manually degraded by the user, or degraded through cavitation generated by the oscillations of the surface, side or tip of the instrument. A further step envisioned incorporates changing the orientation of the instrument to bring a polishing surface in contact with an area of the capsule in need of polishing and polishing the capsule.

BRIEF DESCRIPTION OF THE DRAWINGS

The foregoing and other features of the present invention will be more readily apparent from the following detailed description and drawings of an exemplary arrangement of the elements of the instrument described in which:

FIG. 17B illustrates a comparison of a side cutaway view of the cortex removal and capsule polishing instrument detailing the channels of FIG. 2 and a side solid view of the same.

DETAILED DESCRIPTION OF THE INVENTION

Figure 1:
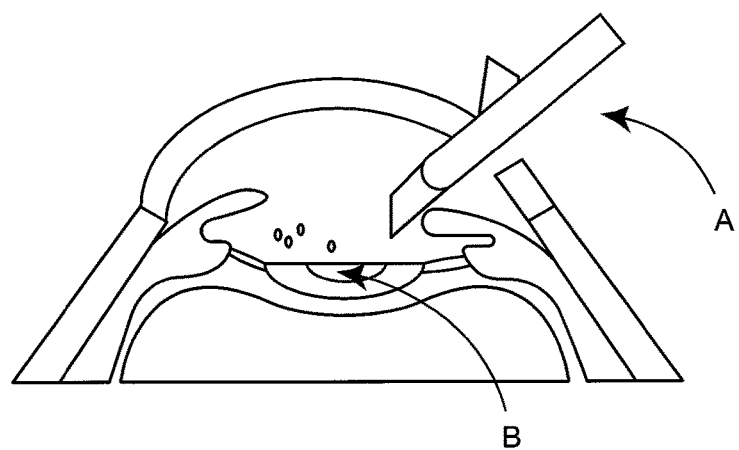
FIG. 1 illustrates prior art procedures for cataract surgery.

The present invention is directed to the assisted removal of the cortex, capsule polishing and destruction/removal of other intraocular structures. By way of overview and introduction, the instrument and method disclosed herein provides for a configuration selectable instrument which allows one of ordinary skill in the art to remove the cortex and polish the lens capsule using an instrument configured to oscillate. For example, the described instrument employs the use of an ultrasonic energy transducer to oscillate the instrument. Specifically, the instrument and method of the present invention are configured to use an oscillator to vibrate an endpiece portion of the instrument to ensure the disruption of the cortex during a cataract removal procedure, as well as the dislodging of epithelial cells from the lens capsule. Furthermore, the present invention is directed to the use of an oscillating abrasion tip, surface or feature which is integral to the endpiece of the described invention. In one configuration, this polishing surface is configured in order to achieve the purposes of polishing the capsule during a cataract removal procedure.

The present invention described provides for an instrument which reduces the possibility of damaging the delicate structures of the ocular cavity, by preventing compete occlusion of an inlet by intraocular tissues. Furthermore, the instrument described reduces the need to repeatedly insert and remove various instruments and devices into the eye during a surgical procedure. As such, through the use of the described instrument and method, the incidence of post-surgical infection is significantly reduced.

While the instrument herein described is envisioned in one operative mode to engage in oscillation at ultrasonic frequencies, the present invention may also operate at frequency ranges lower than ultrasonic or higher than ultrasonic. For example, the present invention may operate at a frequency range from below 10 HZ to above 40 KHz.

In the illustrated embodiments, the instrument depicted is equipped with elements that enable the instrument to accomplish both a cortex degrading function, as well as a capsule polishing function, with an optionally removable endpiece. In one configuration, the endpiece is used for degrade the cortex and/or nucleus and capsule polishing or any combination thereof. In this arrangement, the endpiece is of solid body construction and does not incorporate an inlet or aspiration port.

Those skilled in the art will quickly appreciate that the endpiece which incorporates, the functions of both the cortex removal or the combined cortex removal and capsule polishing are separable and can be undertaken as discrete independent instruments. Those skilled in the art will recognize that the endpiece can be configured as an arrangement of elements, each element designed to perform or undertake a specific function. For example, the endpiece of the described instrument is configurable with removable surfaces, tips, or structures to assist in performing the desired functions. The invention as provided is in no way limited to the description as provided in the figures and the subject matter thereof is applicable to any obvious modification and arrangements of those described.

FIG. 1 depicts a prior art phacoemulsification procedure conducted with an ultrasonic cutting hand tool A. The hand tool possesses all the necessary electrical, conductive and material linkages to any control center. Also, pumps are provided and incorporated herein as necessary. In this depiction the cataract B and its particles are broken up and removed from the eye cavity through passages in the tool A.

Figure 2:
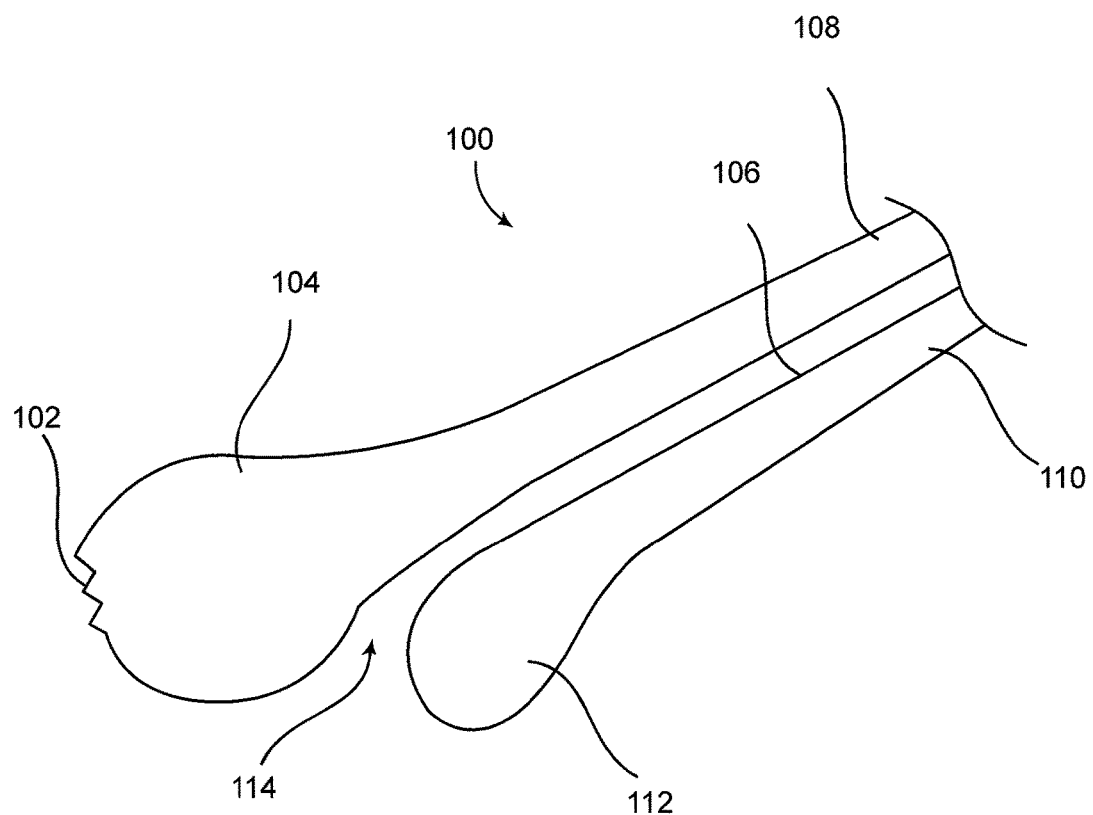
FIG. 2 illustrates a side view, partially cutaway, of the combined cortex removal and capsule polishing instrument according to an embodiment of the present invention.

As illustrated in FIG. 2, the present instrument provides for a surgical instrument equipped with an endpiece 100. The endpiece incorporates a bifurcated tip or surface structure 104, 112. The endpiece 100 further possesses a channel 106 between the two tips or surfaces. In one arrangement of elements, the structure 104 of the instrument is a primary polishing surface. This surface is configured to polish the capsule after the cortex has been removed. In an exemplary configuration, the polishing surface 104 is equipped with abrasive element 102, which is used to physically abrade cells from the capsule lining. For example, the polishing action accomplished by the illustrated instrument is sufficient to remove strands of cortex still attached to the capsule, anterior and posterior as well as polishing the anterior and posterior capsule, depending on the conditions of the capsule after cortex removal. It is envisioned that the abrasive element 102 is formed out of the same material as the polishing tip 104. For example, the depicted elements are capable of being formed out of metal, plastics, composite material or other suitable synthetic materials capable of performing the actions and function described herein. In the alternative, the abrasive element 102 may be formed of a different material that is specifically selected for the removal of specific lens remnants or other tissues or material that need to be removed from the eye.

As further illustrated in FIG. 2, the instrument 100 is also equipped with an aspiration surface 112, configured to direct and contour the suction of emulsified particles of the cataract into the suction inlet 114 and extracted through channel 106. While the elements of both surfaces are combined in a single instrument as provided in FIG. 2, in an alternative embodiment, the polishing surface 104 and the aspiration surface 112 may be incorporated into separate removable elements of the endpiece. In both instances, the instrument 100 is a removable instrument that is configured to couple to a standard handtool, such as the handtool used in traditional phacoemulsification. In this configuration, any material linkages, pumps and conduits located in the handpiece are connected or otherwise communicated to their respective portions of the endpiece through standard linkages.

In one arrangement of elements, the aspiration surface 112 is used to polish the capsule by operating on a low oscillation setting. In this configuration the instrument provides for oscillations at the low end of the frequency and amplitude range. The instrument described is arranged such that the cortex, as well as the remaining epithelial cells on the capsule surfaces, is removed by suction.

In a further arrangement of elements, both the aspiration surface 112 and the polishing surface 104 are equipped with rounded faces such that no angled surfaces are presented near the suction inlet 114. The tips 112, 104 are configured so as to avoid pointed or jagged edges that could penetrate the posterior capsule causing the capsule to fail and resulting in complications with the procedure.

As depicted in the illustrated arrangement, the inlet 114 is set back from the distal surface of the endpiece 100, which in this case is the distal end of primary polishing surface 114 and the polishing surface 112, such that the capsule tissue is prevented from being sucked directly into the inlet 114 during aspiration or polishing. Likewise, the inlet is equipped with secondary ports, ridges, divots, ports or small communications or openings into the channel 106, or other structures designed to prevent complete occlusion of the inlet by membranous tissues. In a further arrangement of elements, the inlet is configured with mechanisms designed to allow the shape and size of the inlet to be configured by a user. For example, the inlet is equipped with a plurality of baffles actuated by a motor or other mechanism which can alter the diameter of the inlet. In another configuration, a series of elements are provided to selectively alter shape of the inlet by covering portions of the inlet.

This is in contrast to existing ultrasonically powered instruments, which are configured to use ultrasound to cut intraocular structures as opposed to the present invention which is configured to emulsify intraocular structures.

In the present description of the invention, the term emulsify can be used to describe any agitation, disruption, destruction, liquefaction, disintegration, or other destruction of an intraocular structure Through the use of the rounded, recessed inlet 114, the present instrument is configured to avoid puncturing or otherwise lacerating the intraocular structures of the eye.

In one particular arrangement, the position of the inlet 114 is such that the vacuum pressure exerted by the pump is negligible in the area immediately outside inlet 114. In this arrangement, the suction is such that only ambient particles of cortex or epithelial cells in close proximity to the inlet are drawn into the channel 106. Through this configuration, intraocular structures are not significantly deformed if the instrument comes into close proximity. Additionally, by providing minimal suction beyond the surface of the instrument the delicate cells located within the interior of the ocular cavity are not disturbed by large pressure gradients.

In an alternative arrangement, the aspiration surface 112, inlet 114 and channel 106 are each configured with groves, voids, divots, ports or small communications or openings into the channel 106, or other arrangements that prevent complete occlusion by the capsule of the of the inlet. As a result of the vibratory energy, complete occlusion is not necessary to extract the material from the capsule. Thus a safer design of the tip is achieved.

As further illustrated in FIG. 2, the channel 106 is connected to a pump (not shown) configured to extract material that enters the inlet 114 and travels through the channel 106. In the present embodiment, the channel 106 is completely enclosed along the length of the instrument. In this way, the surfaces 104 and 112 form an integral structure with one another encapsulating the channel 106. In this arrangement, the channel and inlet are placed in an asymmetrical configuration relative to the longitudinal axis of the endpiece.

As shown, each surface 104, 112 is supported by a shaft 108, 110 respectively, designed to transmit oscillating vibrations from an oscillator (not shown) located in a base station or the hand-tool itself. In one arrangement the oscillator is an ultrasonic transducer. In another arrangement, the oscillator is a motor. In one arrangement, the motor is electrically powered. In a further arrangement, the motor is operable by compressed fluid such as air or hydraulic fluid. In a particular arrangement of the present invention, the shafts 108, 110 are vibrated such that the corresponding tips 104, 112 are caused to oscillate within as many as 3-axial directions as well as rotate about said axis. In this arrangement, oscillations of the endpiece induce cavitations within the ocular cavity such that the cortex particles are degraded into smaller portions. Alternatively, the cavitations are used to dislodge cells lining the lens capsule.

In the illustrated embodiment the endpiece of the instrument 100 is positioned and secured as an attachment or adaptor to a conventional handpiece A (such as a phacoemulsion tool) such that the endpiece is able to rotate freely about a central axis as well as being configured to be able to laterally slide within a given range along the same axis. In the described configuration, the induced vibrations are sufficient to cause a complete oscillation of the endpiece, or a portion of the endpiece about the 3 axis. Those skilled in the art will appreciate that the vibrations and oscillation rates are configurable for a given situation. As such, it is envisioned that a user will have access to a control mechanism that provides specific oscillation frequencies, period and intensities.

The ultrasonic handpiece from a conventional phacoemulsification technique is configurable to generate the necessary vibrations in the depicted endpiece 100 so as to accomplish the goals provided. In this configuration, the instrument of the present invention is coupled to the handpiece through a screw-thread arrangement, magnetic attraction, pressure valve, spring clasp or any similar mechanism for securing the instrument to the handpiece. In a further arrangement, the conventional phacoemulsification needle is removable, and the instrument of the present invention is inserted in its place. In an arrangement wherein the instrument of the present invention replaces the phacoemulsification tip it, is desirable to match the mass of the instrument to the specific ultrasonic instrument used in the phacoemulsion. In this way, the ultrasonic apparatus does not need to be tuned or otherwise calibrated for the specific instrument.

Figure 3:
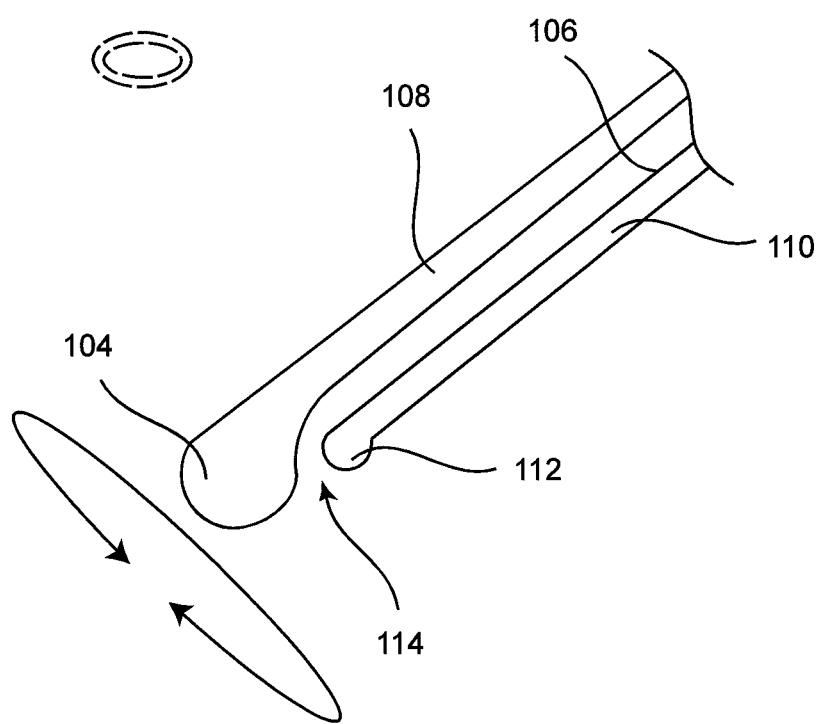
FIG. 3 illustrates a first alternative embodiment of the cortex removal and capsule polishing instrument according to the present invention.

As seen in FIG. 3, an alternative arrangement is provided such that only one surface 104, is configured to be vibrated. In this configuration, the shaft of the aspiration surface 110 is secured such that minimal vibrations are translated to the tip end 112. Thus, the polishing surface is used to abrade cells from the capsule while the inlet 114 is maintained in a relatively stable location. In this manner, more delicate procedures are undertaken.

Figure 4:
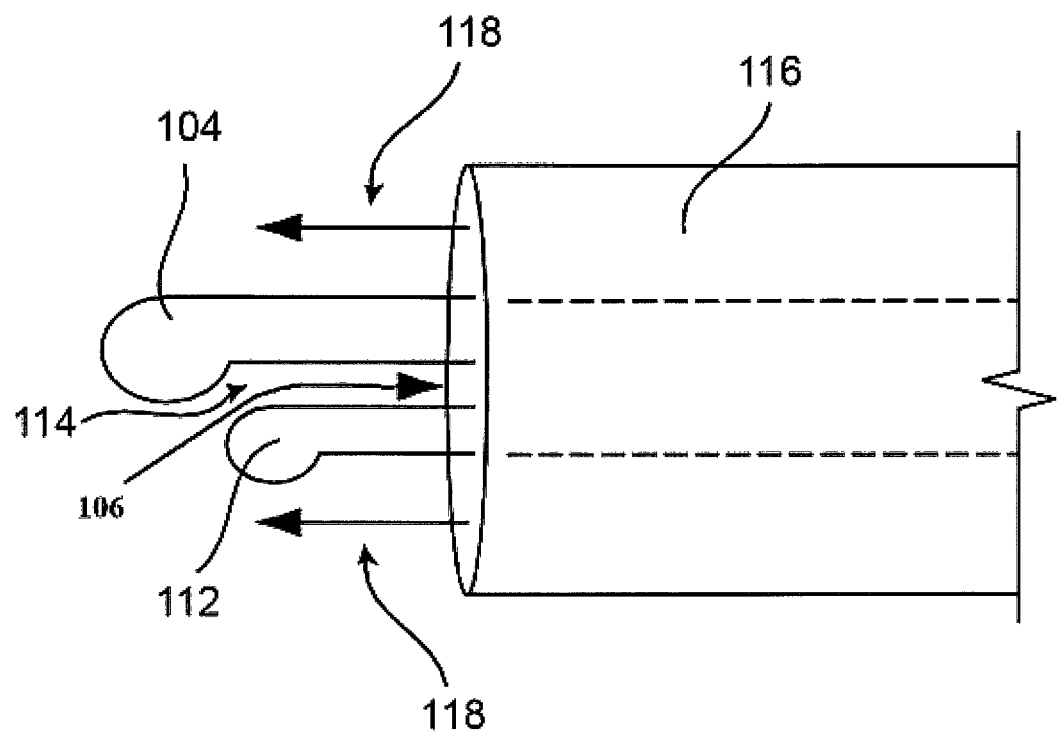
FIG. 4 illustrates the first alternative embodiment of the cortex removal and capsule polishing instrument as shown in FIG. 3, but equipped with an irrigation sleeve according to the present invention.

As further seen in FIG. 4 the surfaces 104 and 112 operate inside the sleeve. The aspiration of the cortex material is directed through the channel 106 and the irrigation is directed into the eye through the sleeve 116 (as indicated by the arrows 118). The irrigation through the sleeve 116 also serves as a cooling fluid jacket for the oscillating tips. As such, the aspiration/irrigation system of the present invention is configurable to cool the instrument during vibration based disruption.

In a further configuration, it is envisioned that the aspiration function of the instrument is selectable such that no material is extracted through the inlet 114. In an alternative arrangement, when engaged in abrading or dislodging unneeded tissue that needs to be removed from the eye, the channel 106 is used to direct fluid into the optical cavity. In a further configuration arrangement, the inflow of fluid is directed from the irrigating sleeve 116, or from a second instrument introduced into the eye through another incision during a procedure employing a bimanual technique. Alternatively, the fluid is withdrawn through the sleeve 116.

In a still further alternative arrangement, the polishing surface 104 is fitted with a covering or enclosure designed to fit over the surface 112 or the inlet 114. In this configuration the covering (not shown) is equipped with a sponge or visco-elastic material deigned to gently remove material from the capsule surfaces. In an alternative configuration, the sponge surface is directly incorporated into the handpiece previously described.

In still a further configuration, the handpiece is configured so as to transmit and receive information through tactile means. For example, the handpiece so described is configured with a pressure sensor so as to increase or decrease the amount of vibratory energy and/or negative pressure transmitted to the tip based on the pressure exerted by the user on the grip. Likewise, the presence of materials within the eye is transmitted to the handpiece as a series of actuated nubs or nodules. For instance, the capsule in direct proximity to the tip is represented by an increased height of an actuated nub or ridge co-presence of the extensive with the handpiece. In one configuration, the handpiece is wirelessly connected to a control station using commonly understood wireless protocols.

As described in the foregoing, the present invention is directed to an instrument and method for polishing lens capsule, cortex emulsification and emulsification of other tissues in need of removal from the eye, with or without irrigation and aspiration, and with or without mechanical agitation either by an operator or an agitation instrument.

Figure 5A:
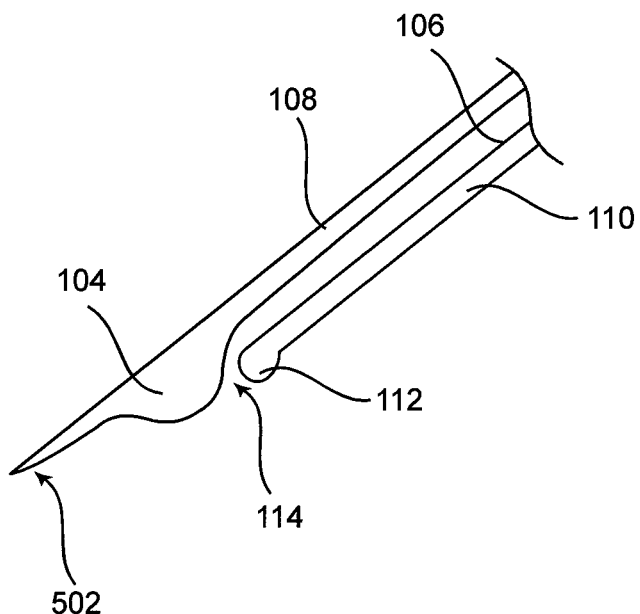
FIG. 5A-5C illustrates alternative embodiments of the cortex removal and capsule polishing instrument of the present invention.

As seen in FIG. 5A, the instrument 100 so described may be equipped with an emulsifying surface 502. In this arrangement the emulsifying surface 502 is configured such that at a given orientation the tip is placed in contact or close proximity with the nucleus and is able to degrade it. In an alternate orientation the emulsifying surface 502 is positioned such that the polishing surface 104 or the aspiration surface 112 is the primary working surface and there is no danger that the surface 104 will be able to lacerate the capsule. In one configuration, each of the surfaces is placed equidistant from one another around the circumference of the channel 106 such that rotating the instrument 100 is sufficient to engage or disengage a particular function.

Upon activation, the movement of the aspiration surface 112 is used to agitate the cortex so as to break its structure down to render removal easier. In the given operation, the ultrasonically powered instrument first agitates the cortex to disrupt it, allowing for safer removal. Alternatively, the invention is configurable such that the aspiration surface 112 directs cortex material into the inlet 114, and then mechanically degrades, at ultrasonic speeds or otherwise degrades it prior to transporting the material through the channel 106 to the pump.

In a further configuration, the present invention is directed to an embodiment that provides irrigation functions through a sleeve 116, and aspiration functions are provided through the center of the tip, e.g., inlet 114 as shown in FIG. 4. Alternatively, the instrument is configurable for reverse flow, such that irrigation is provided through the channel 106 and inlet 114, while aspiration is through the sleeve 116 or another, second instrument. Additionally, it is possible and envisioned that a simple leakage of fluid is balanced by introduction of liquid into the eye such that is enough to balance the loss of liquid.

Figure 5B:
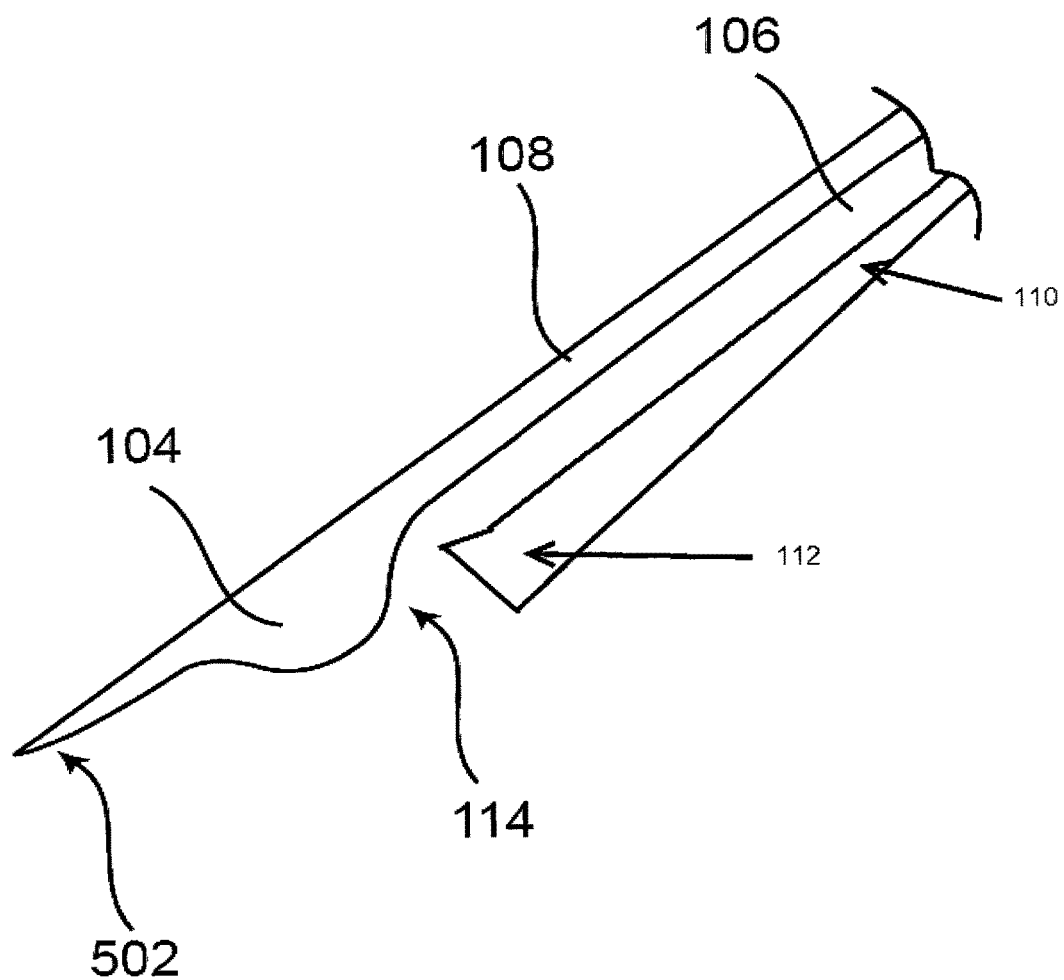

As seen in FIG. 5B, the instrument may be equipped with an emulsification structure, such as a tip, surface or ridge 502. In this arrangement emulsification structure 502 is configured such that at a given orientation the structure is placed in contact with the nucleus and is able to degrade it. In an alternate orientation the emulsification structure 502 is positioned such that the polishing surface 104 or the aspiration surface 112 is the primary working surface and there is no danger that the polishing surface 104 will be able to lacerate the capsule. In this configuration the inlet interior diameter of the inlet is decreased to a minimum size effective such that the likelihood of tissue introduction into the inlet is further minimized.

Figure 5C:
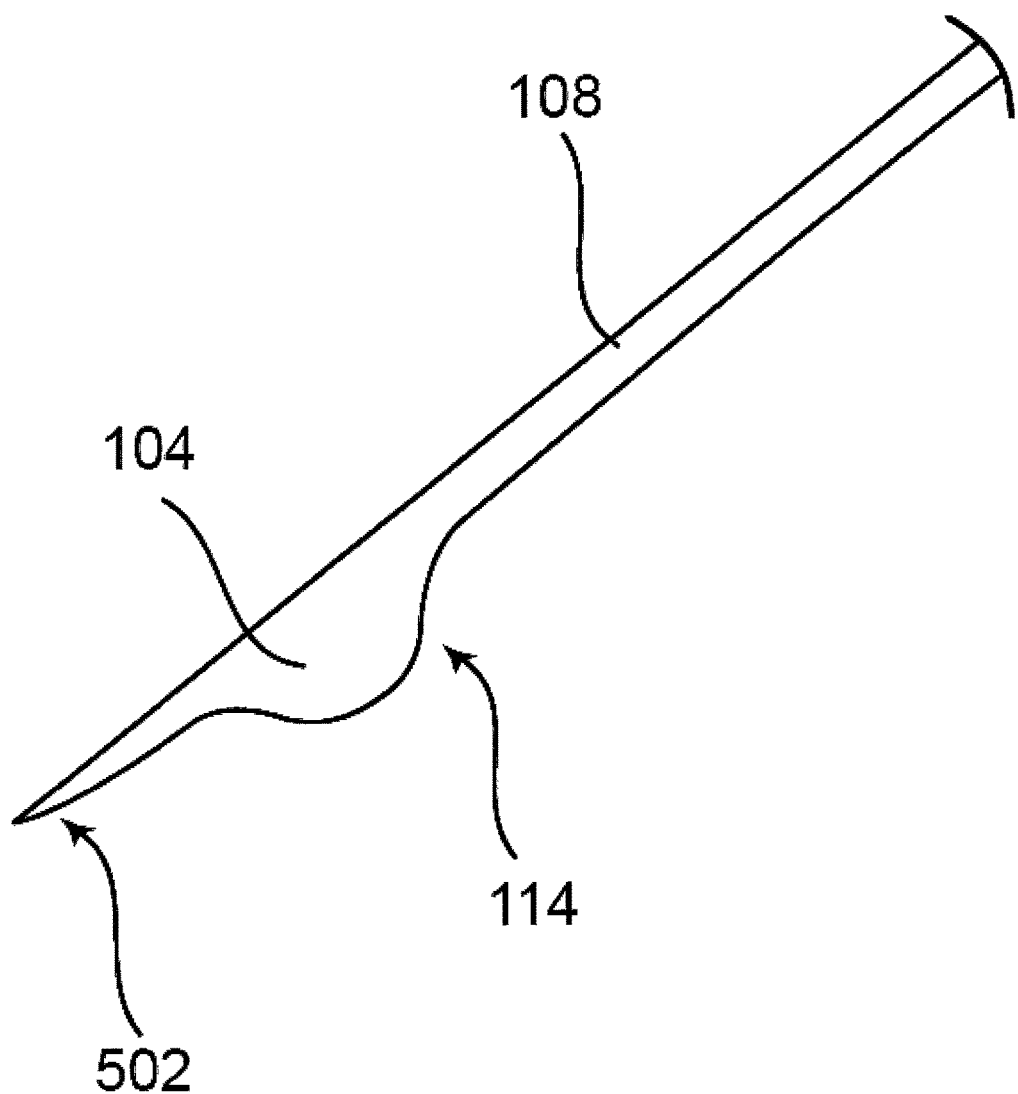

As seen in FIG. 5C, the instrument is only equipped with a phacoemulsification surface 502 and no internal inlet. In this configuration, the surface 502 may be used in conjunction with a second aspiration instrument to insert or withdraw fluid into the eye. Likewise, the surface illustrated can be configured with a water jacket or other instrument to prevent the accumulation of thermal energies during mechanical vibration.

With the configuration of FIG. 4, the irrigation sleeve 116 is used to direct fluid, such as a balanced salt solution, into the eye to maintain equilibrium with the amount of fluid removed through the inlet 114. Through the use of vibrations to degrade the cortex, the needed amount of inlet suction pressure is greatly reduced. As a consequence the amount of fluid introduced into the eye is lowered, since the amount of fluid removed is decreased.

Figures 6A, 6B:
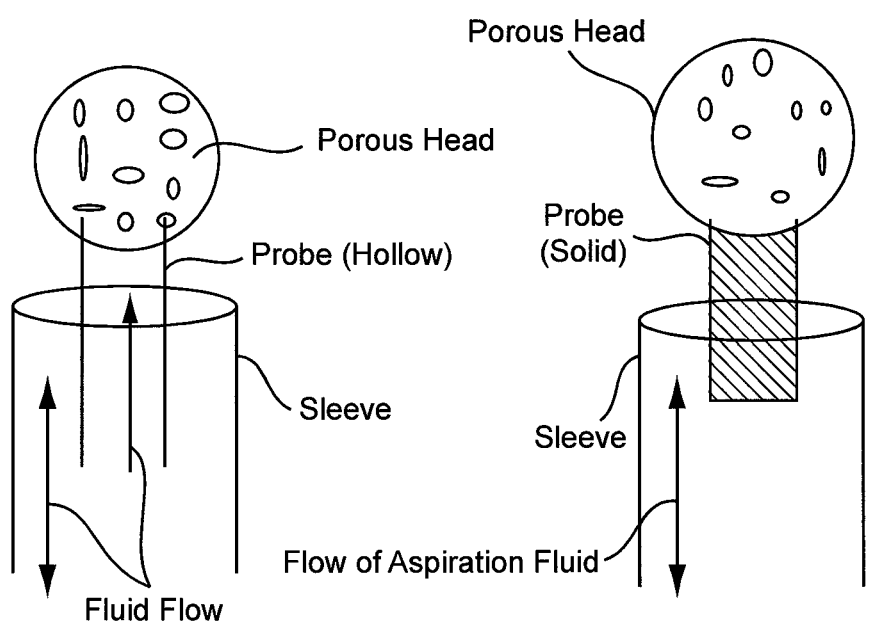
FIGS. 6A and 6B illustrate modified surface portions of the cortex removal and capsule polishing instrument of the present invention.

As seen in FIGS. 6A and 6B, the capsule polishing and removal instrument already described is additionally configured with a porous, pliable structure. For example, a sponge or sponge-like probe material is affixed to the end of the endpiece, or a structure integral to the endpiece, which is formed of either hollow or solid material, such as metal, plastic or composite forms. In the illustrated embodiment the probe is flexible such that it provides resistance, but mechanical give, when placed under compressive pressure. As seen, the porous material is attached to the endpiece through a connector structure. In a further embodiment, the user will move the instrument inside the capsular bag and dislodge the lens material that is attached to the capsule.

In a further configuration, the endpiece is equipped with a volume variable material. This volumetric expansion or contraction can be due, in one embodiment, to changes in the temperature found at the surgical site. In another arrangement, the volumetric change is due to external force or pressure being applied or removed from the material. In a further arrangement external force or pressure can be exerted to reduce the volume of the material for easy extraction from the eye.

In one arrangement, the instrument of the present invention is equipped with a sponge or a special design that it would allow it to expand. In this configuration, the reduced volume would allow for easier introduction into the eye. Once inserted, the expansion would make polishing and removal easier.

Figure 7:
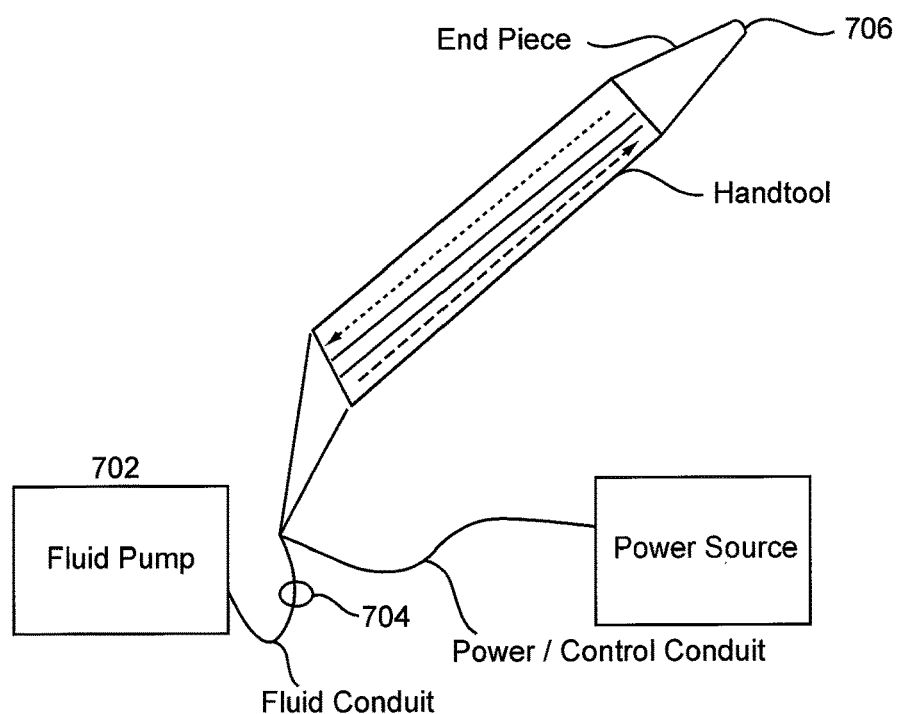
FIG. 7 illustrates an alternative embodiment of the cortex removal and capsule polishing instrument of the present invention.

In another configuration as shown in FIG. 7, a microprocessor controlled pump 702 and valve 704 are used to calculate the specific fluid exchange such that the velocity and volume of the fluids extracted (dashed lines) and introduced (dotted lines) are relatively matched. It is envisioned that the microprocessor is equipped with sensors 706 to detect the overall pressure in the ocular cavity and is configured to control the operation of the pump automatically.

Furthermore, because the pupil is always smaller than the diameter of the lens, (in the case of cataract extraction, which involves the removal of the entire contents of the lens capsule: part of the anterior capsule, nucleus, cortex and capsule polishing), the surgeon cannot visualize the area under the iris, and is thus not able to see if the entire nucleus and cortex have been removed and the capsule is free of epithelial cells.

After the "cataract" has been removed, an intraocular lens implant, known as an IOL or just lens implant, is placed in the capsular bag. Again, since the haptic, (haptic instrument elements are parts of the lens implant that extend into the capsular bag and into the area where the anterior and posterior capsule meet) extend under the iris, it is not possible to examine the exact placement and location of the IOL. Unable to perfectly and completely visualize the IOL, the surgeon may be lulled into believing that that IOL is in the proper position when in reality it may not be.

During surgery in the posterior pole of the eye, that is surgery below or further and deeper into the eye, past the lens, the surgeon has to be able to see through the cornea and the lens (if it has not been previously removed) or the posterior capsule (if the patient had cataract surgery prior). If the cornea and lens are clear at the start of the operation, they often become cloudy during the operation, presenting serious challenges to the surgeon. Other structures that may also interfere with the surgeon ability to see are coagulated or fresh blood and vitreous strands and membranes.

All of the above detail why having an alternative way of visualizing the contents of the eye during eye surgery is vital for a successful operation.

Therefore an instrument and method of visualization inside the eye, inside the capsular bag before and after the IOL has been placed inside the eye, visualization of the posterior pole through blood, vitreous strands and membranes, near the periphery of the retina would be of great value in making eye surgery safer, more successful, faster, and with fewer complications. Such visualization can be achieved through the use of a fiber-optic "pipe" to allow for illumination, visualization or oscillation, or a combination of all three functions.

Figure 8:
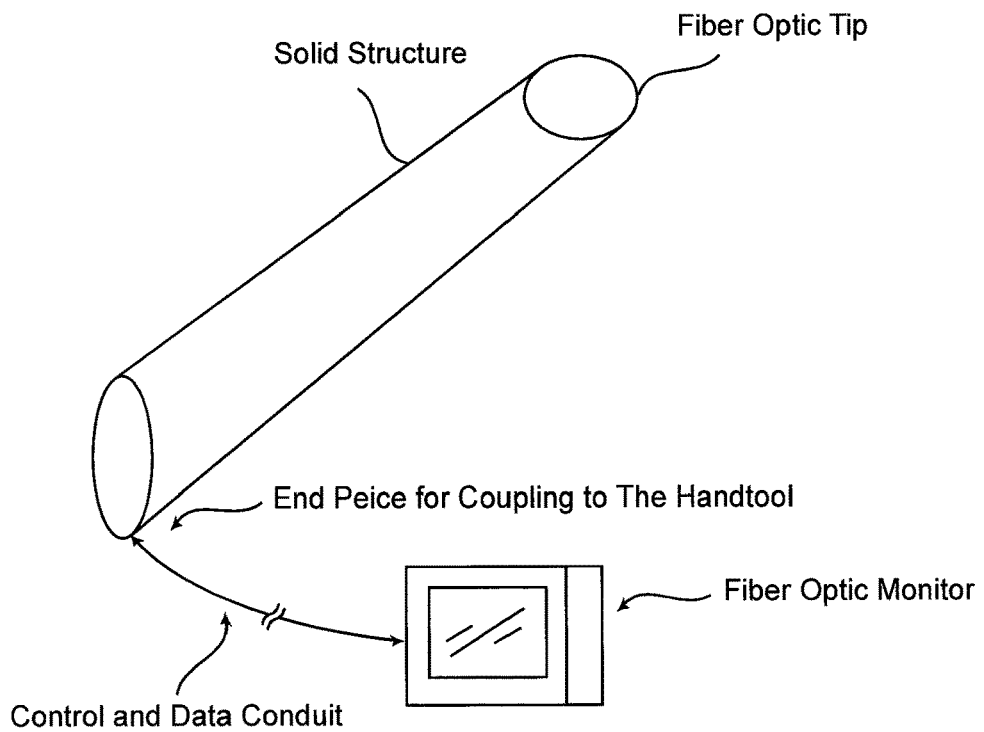
FIG. 8 illustrates an alternative embodiment of the cortex removal and capsule polishing instrument of the present invention.

As shown in FIG. 8 the ophthalmic instrument includes a fiber-optic imaging attachment secured to the endpiece. In a further arrangement, fiber optic lighting and optical conduits are integrated into the endpiece so as to provide visual confirmation of the conditions of the tissues. In this arrangement, the fiber optic attachment includes a mirror element that directs light at an angle sufficient to illuminate the intraocular structures regardless of orientation or positioning.

Furthermore, the fiber optic attachment is also equipped with a stand-off section or ring that prevents the fiber optic portion of the instrument from coming into direct contact with intraocular structures. In a further embodiment, the fiber-optic portion of the endpiece is fully integrated into the capsule polishing or cortex emulsification instrument as described previously. In a further configuration the stand-off ring can be used to degrade the cortex material or polish the capsule This imaging instrument can be either a fiber optic cable or an instrument configured to transmit images via a fiber optic conduit. In one configuration the image information and data is transmitted to a video display monitor. In another configuration, the data is converted and transmitted wirelessly from a transmitter integral in the handpiece to a properly equipped display instrument. In a further arrangement, control data is transmitted to control the power of the oscillations via the fiber optic conduit.

The fiber-optic attachment can be used directly to emulsify the cortex or intraocular structures either through direct or mechanical emulsification. The fiber-optic instrument can be used to allow the user to view the posterior pole of the eye, and be used to breakdown blood, membranes and other tissues. The fiber optic instrument is configurable such that the images provided to the operator are electronically synchronized with the oscillations of the instrument. In this configuration, the operator is able to simultaneously observe intraocular structures and preform cutting or emulsification/destruction actions on intraocular structures. Furthermore, the fiber-optic attachment is configurable to provide a variable light intensity illumination to the surgical site without the need to provide visual information to the user.

Figure 9:
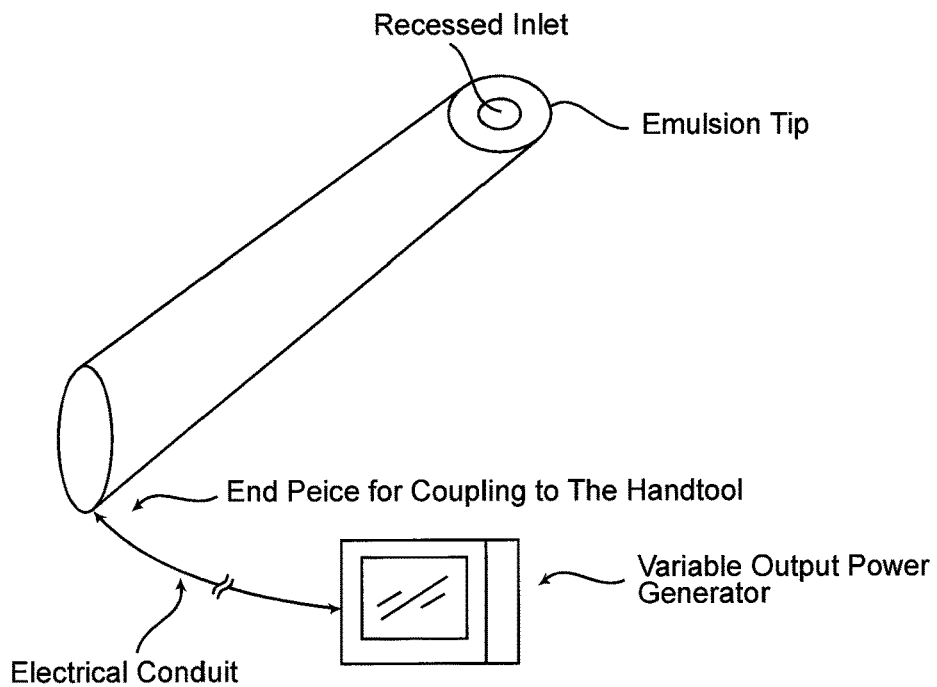
FIG. 9 illustrates an alternative embodiment of the cortex removal and capsule polishing instrument of the present invention.

As shown in FIG. 9, the power used to generate the vibration of the endpiece with or without an incorporated fiber optic attachment, is selectable and available at different settings based on the need of the operator.

Figure 10:
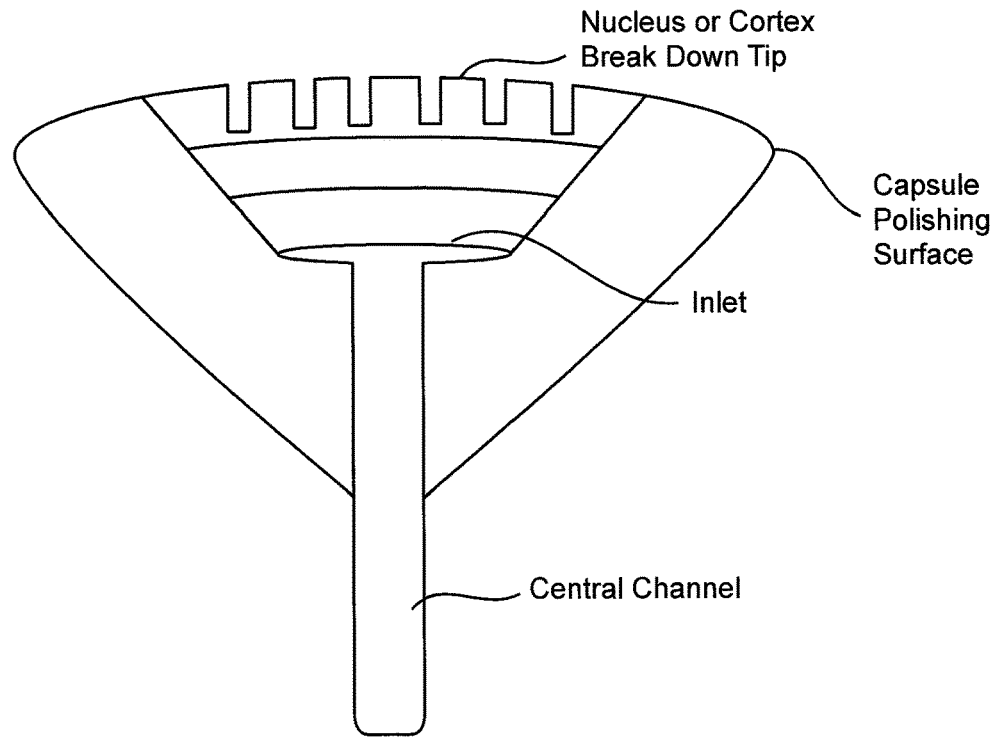
FIG. 10 illustrates an alternative embodiment of the cortex removal and capsule polishing instrument of the present invention.

As shown in FIG. 10, any of the endpieces so described are, in one arrangement, configurable with a recessed fluid inlet or outlet and a series of ridges, divot, ports or small communications or openings into the channel 106, or other structures designed to dislodge cortex or other material, while preventing damage to the capsule and other eye structures. In this arrangement, the endpiece functions both to polish the capsule and to dislodge cortex material.

Figure 11:
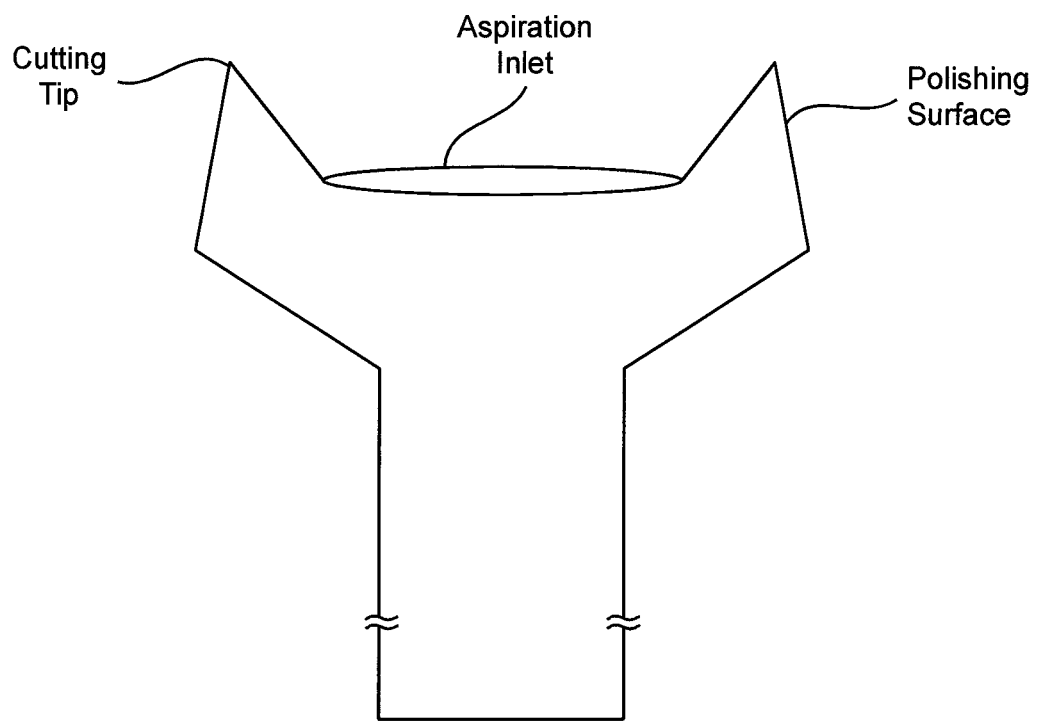
FIG. 11 illustrates an alternative embodiment of the cortex removal and capsule polishing instrument of the present invention.

As shown in FIG. 11, these endpieces are further, or in the alternative, configurable with a recessed fluid inlet or outlet and a cutting head that is configured to disrupt, dislodge or otherwise destroy cortex or other material, while preventing damage to the capsule and other eye structures. In this arrangement, the endpiece also functions to both dislodge cortex material and polish the capsule.

Figure 12:
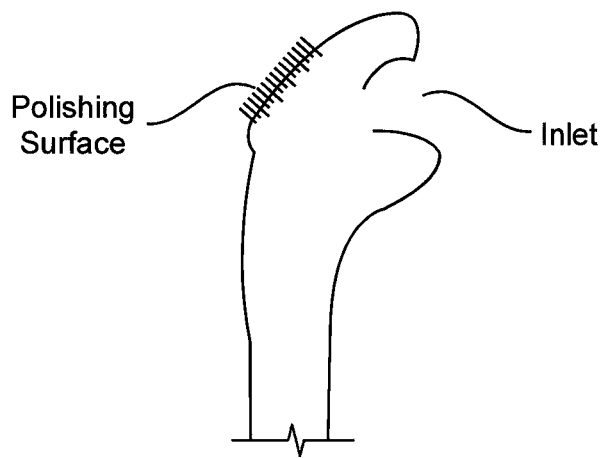
FIG. 12 illustrates an alternative embodiment of the cortex removal and capsule polishing instrument of the present invention.

As shown in FIG. 12, these endpieces further, or in the alternative, are equipped with a recessed fluid inlet or outlet and only a polishing surface designed to polish the capsule or other eye structures. In this design, the recessed inlet is configured to reduce the likelihood of damage to the eye structures due to the complete occlusion of the port by intraocular tissues. The polishing surface is equipped with divots, groves, or structured recessed areas designed to dislodge cortex material and polish the capsule.

The described solid or hollow endpiece is equipped with any number of angles or bends such that a portion of the endpiece is able to access every portion of the capsular bag (for example, through 360 degrees of rotation).

As further provided, the endpiece is configured to either be used in a power assisted or unassisted activation state. For example, the present invention can simply be engaged by manually dislodging material from the capsular bag. In the alternative, the described endpiece can be coupled to existing, or subsequently designed mechanical or ultrasonic instruments that allow the endpiece to be oscillated along the length of the probe and/or in along three additional axes.

The porous material, while herein defined as a sponge material, can be formed from any material that is soft, pliable, porous and easily compressible. In one arrangement of elements, the probe is a hollow tube that allows fluid to be directed through the probe and out through the porous material through the use of a pump. Alternatively, the present instrument is equipped such that material may be withdrawn from the capsular bag through the porous material and directed out through the hollow probe through the use of a similar pumping instrument.

In yet a further embodiment, the probe is a configured to be a solid shaft, but is equipped with an aspiration sleeve or cooling jacket, configured to direct or withdraw fluid into the capsular bag.

Additionally, the invention so described can be applied in conjunction with or as a modification of, fiber-optic imaging instruments. It is important to note that during cataract surgery, the surgeon looks inside the eye through an operating microscope. The field of surgery is illuminated by light that is paracentral to the visual axis of the surgeon. The cornea often acts as a mirror causing glare and difficulty seeing inside the eye. Other structures such as drapes, conjunctivae, sclera can also cause reflective glare. Past studies and reports have demonstrated that prolonged exposure of the eye to the powerful microscope light can cause permanent damage to the macula, a vital structure for clear vision.

Thus, in order to see inside the eye the surgeon has to have, first of all, a clear view through the cornea. However, because of age and disease, the cornea is or becomes cloudy during the operation and thus a major challenge to successful, safe surgery because the intraocular structures become difficult to see.

Figure 13:
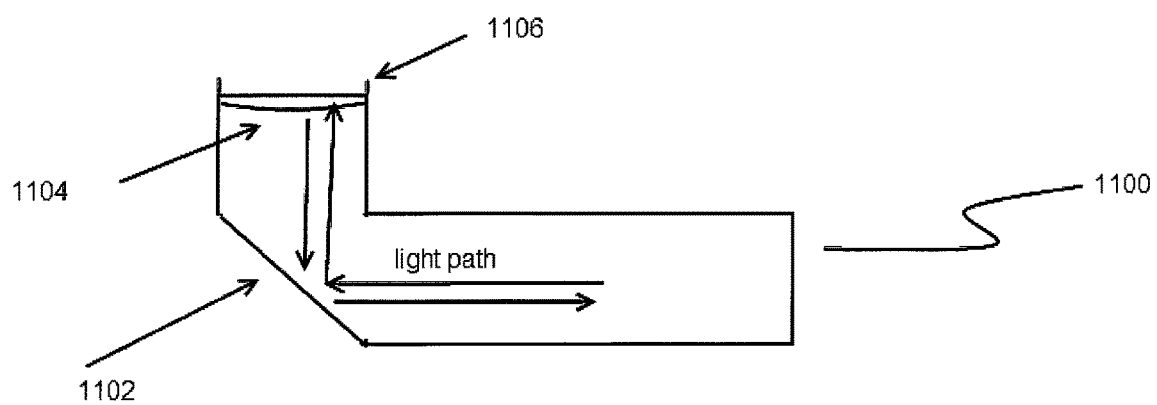
FIG. 13 illustrates alternative arrangement of the instrument of the present invention.
Figure 14:
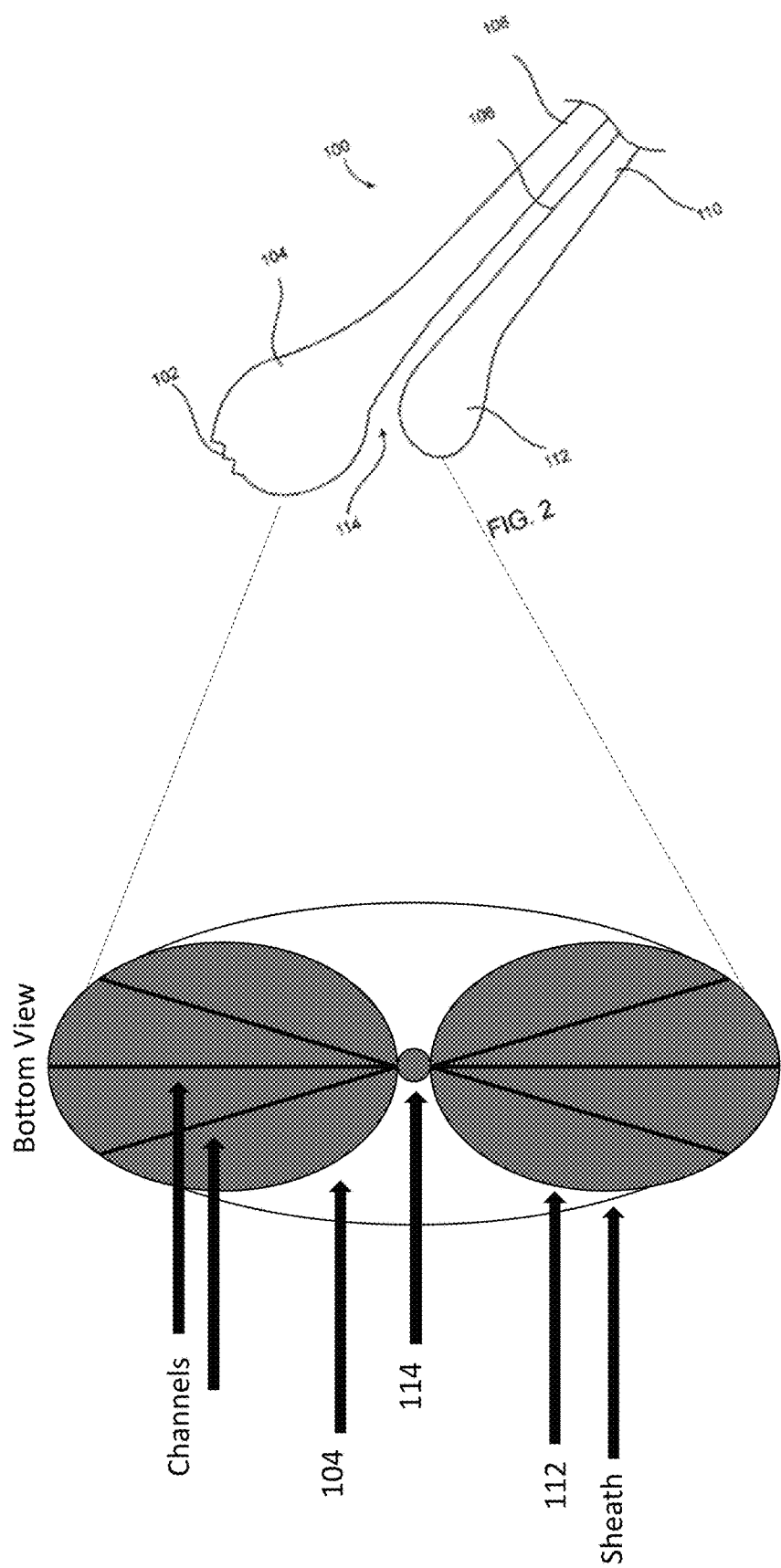
FIG. 14 illustrates a bottom view of the cortex removal and capsule polishing instrument of FIG. 2.
Figure 15:
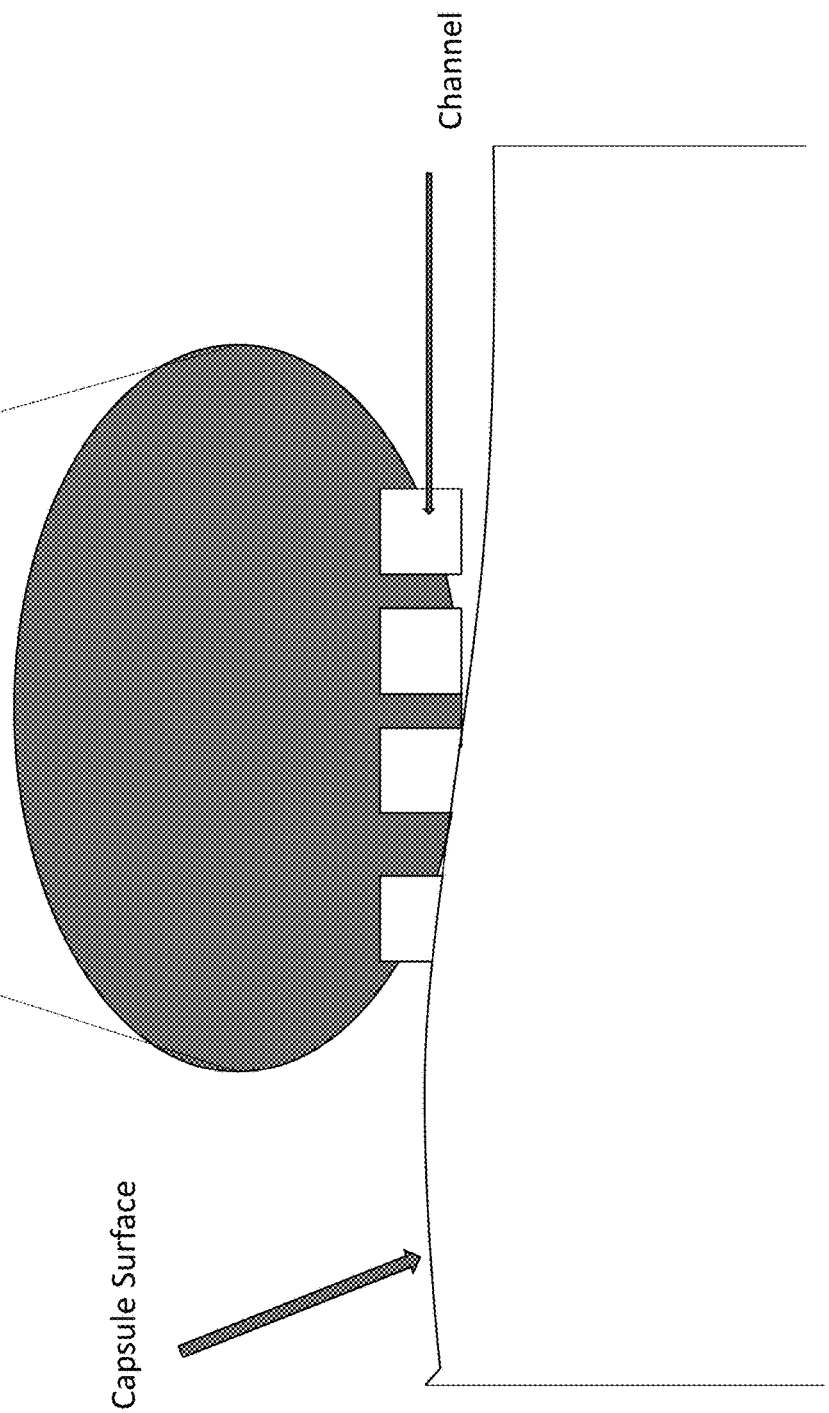
FIG. 15 illustrates a front view of the cortex removal and capsule polishing instrument of FIG. 2.
Figure 16:
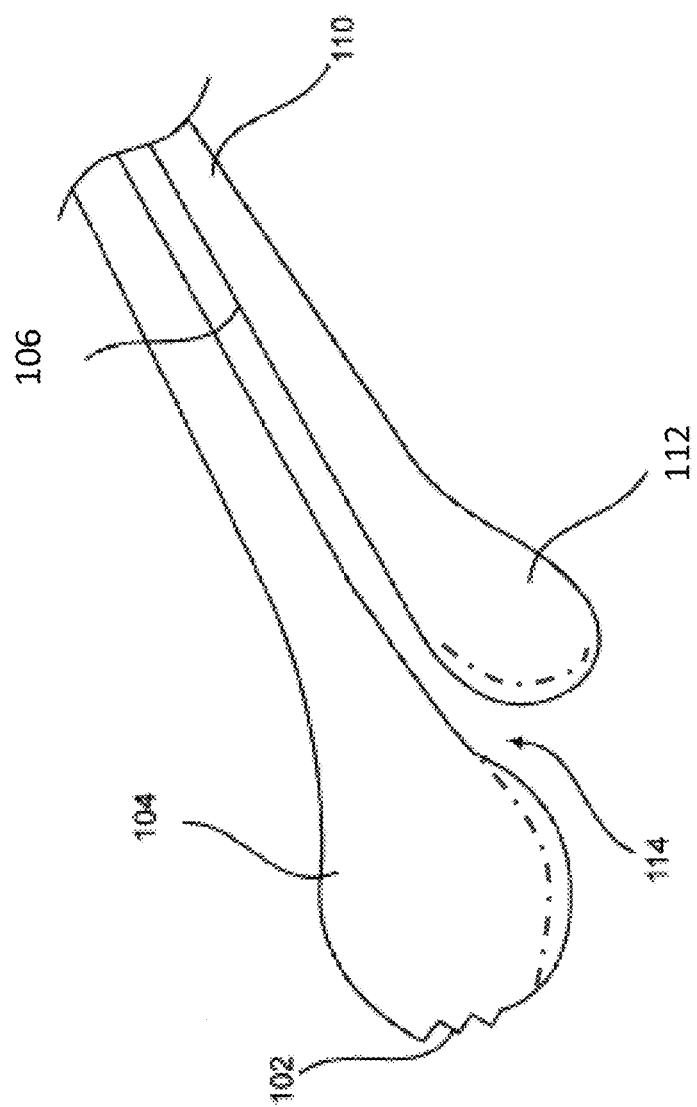
FIG. 16 illustrates a side cutaway view of the cortex removal and capsule polishing instrument of FIG. 2
Figure 17A:
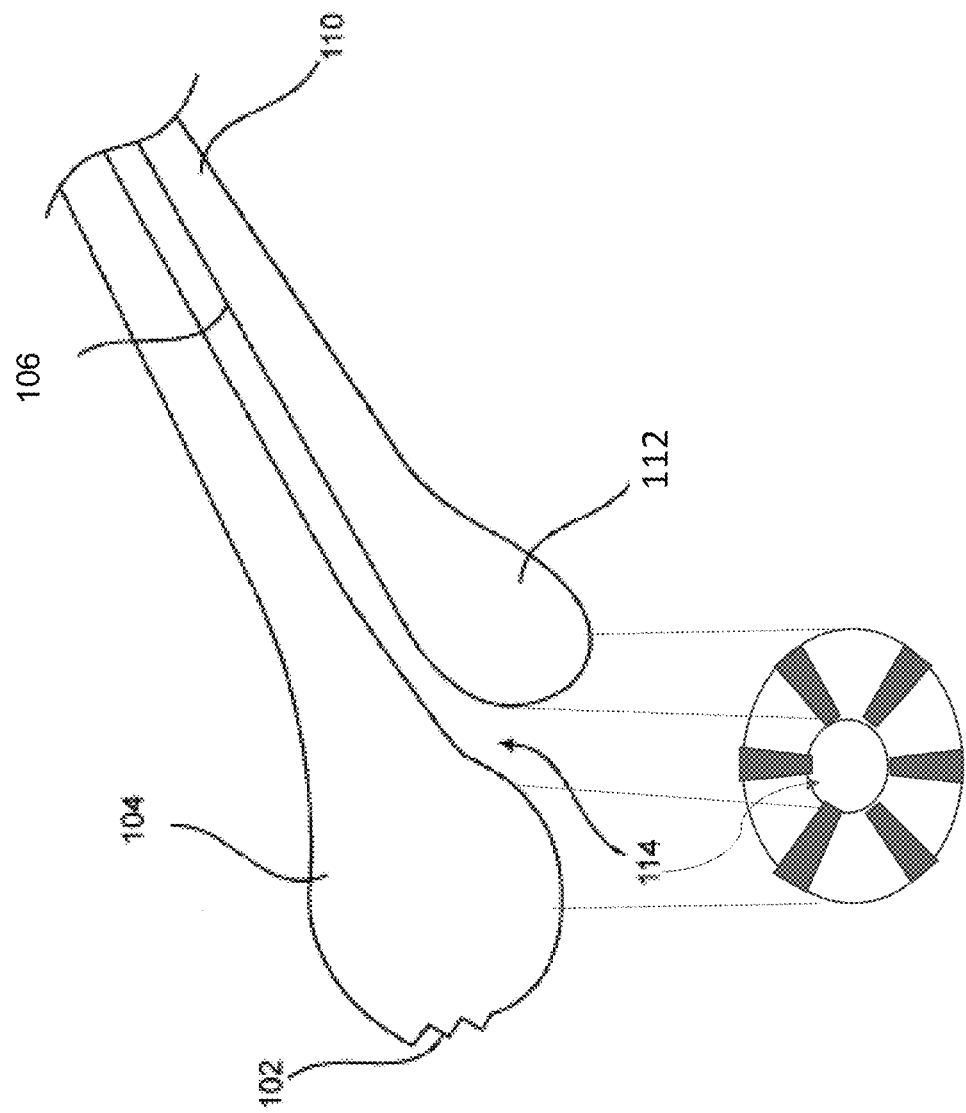
FIG. 17A illustrates a bottom detailed view of the channel of the embodiment of the cortex removal and capsule polishing instrument of FIG. 2.
Figure 17C:
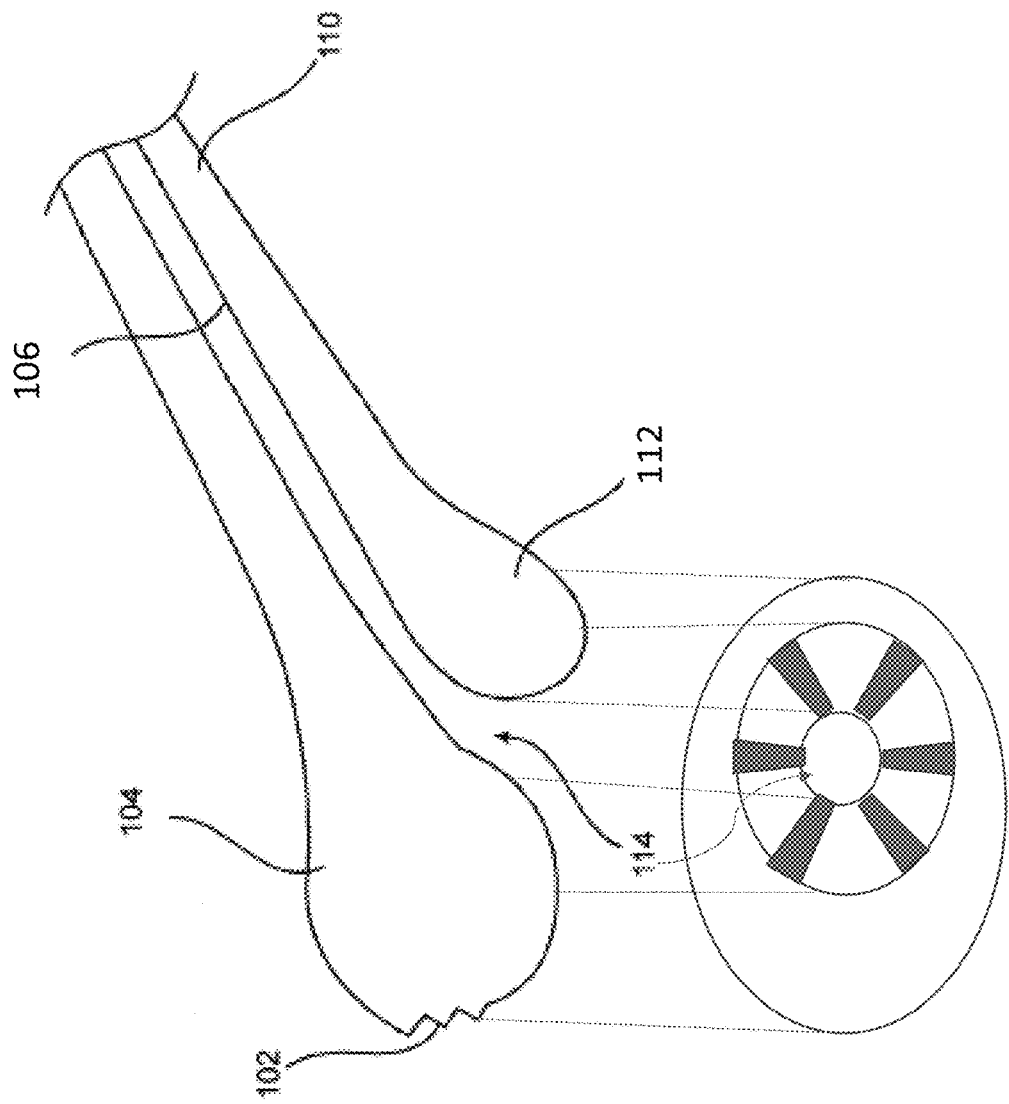
FIG. 17C illustrates top detailed, cutaway view of the channel of the cortex removal and capsule polishing instrument of FIG. 2.

As further shown in FIG. 13, the fiber optic pipe 1100 is arranged such light directed into the eye is reflected off of intraocular structures and transmitted back though the fiber-optic pipe 1100 to the operator. In this configuration, a mirror 1102 is used to direct light such that images of structures out of the field of vision of the operator are transmitted to the operator. In one arrangement, the mirror is controllable, such that the angle of reflection can be changed to view a greater range of intraocular structures. It should be appreciated that the fiber-optic pipe describe can be equipped with ridges, divots or other structures 1106 to abrade intraocular structures. Likewise, the fiber-optic pipe is configurable to be mechanically vibrated to emulsify intraocular structures. The fiber optic pipe is further equipped with a lens 1104 to focus light and produce viewable images. In one arrangement, the lens is a variable focus lens or collection of lens elements. The images from the fiber-optic pipe can be transmitted to a user directly, or to an image or video processor prior to display to a user. Furthermore, the fiber-optic pipe is equipped with a sleeve for irrigation or aspiration of fluid in the eye.

It should be understood that the fiber-optic instrument so described is configurable to perform illumination, visualization and emulsification or cutting functions, or some combination thereof.

In any of the foregoing embodiments, it is envisioned that aspiration sleeves or irrigation mechanism can be integrated into the design so as to allow the described probe and tip to accomplish those same functions.

It should be understood that various combinations, alternatives and modifications of the present invention could be devised by those skilled in the art. The present invention is intended to embrace all such alternatives, modifications and variances that fall within the scope of the appended claims.

While the invention has been particularly shown and described with reference to preferred embodiments thereof, it will be understood by those skilled in the art that various changes in form and details may be made therein without departing from the spirit and scope of the invention.

What is claimed:

1. An ophthalmic surgical instrument for use at a surgical site, comprising:
    an endpiece configured to be operable with a handpiece having at least one axis, said endpiece configured to oscillate about the at least one axis;
    wherein the endpiece is configured with an inner channel there through, at least one polishing surface, a portion of the at least one polishing surface, where a portion of the polishing surface is in communication with the inner channel and configured with a plurality of recessed channels, at least a portion of the polishing surface is equipped with an abrading element extending from at least a portion of the polishing surface in a first direction, and at least one aspirating surface, where a portion of the aspirating surface is in communication with the inner channel and equipped with recessed channels; wherein a portion of the aspirating surface is configured to emulsify intraocular structures and at least a portion of the aspirating surface is configured to extend in a direction orthogonal to the first direction; and
    an inlet defined by the portion of the polishing surface and aspirating surface in communication with the inner channel and
    wherein said polishing surface is configured to polish the lens capsule of the eye.

2. The ophthalmic instrument of claim 1, wherein the emulsification surface and polishing surface have rounded faces.

3. The ophthalmic instrument of claim 1, wherein said endpiece is configured to oscillate so as to induce cavitation within a fluid present in the surgical site.

4. The ophthalmic instrument of claim 1, wherein said apparatus has the ability to selectively extract material from the eye.

5. The ophthalmic instrument of claim 1, wherein the endpiece having at least one of said polishing surface and emulsification surface is configured to selectively oscillate along three axis.

6. The ophthalmic instrument of claim 5, wherein at least one of said polishing surfaces and emulsification surfaces has the ability to rotate around a central axis of the endpiece.

7. The ophthalmic instrument of claim 6, wherein at least a portion of the endpiece is configured to oscillate at a variable frequency setting.

8. The ophthalmic instrument of claim 7, wherein the endpiece is selectively removable from the handpiece.

9. The ophthalmic apparatus of claim 1 further including;
    a selectable power source for generating the oscillation of the endpiece.

10. The ophthalmic instrument of claim 9 wherein the endpiece is equipped with a plurality of emulsification and polishing surfaces, each surface configured to be selectably oscillated independently of any other surface.

11. The ophthalmic instrument of claim 1, wherein the abrading element is a compressible, porous material having suitable durability to abrade the interior of a capsular bag.

12. The ophthalmic instrument of claim 9, further comprising a sheath surrounding the endpiece, the sheath being equipped with at least one outlet to introduce material to, or remove material from the eye.

13. The ophthalmic instrument of claim 12, wherein the endpiece is formed of a solid resilient material.

14. The ophthalmic instrument of claim 9, wherein the endpiece further includes a fiber-optic imaging instrument configured to transmit images from the surgical site to the operator of the surgical instrument.

15. The ophthalmic instrument of claim 11, wherein the volume of the porous material is dependent on ambient temperature.

16. The ophthalmic instrument of claim 9, wherein the endpiece is configured to articulate in three directions about a longitudinal axis of the handpiece.

17. The ophthalmic surgical instrument of claim 1, wherein a diameter of the inlet of the endpiece is variable.

18. The ophthalmic surgical instrument of claim 1, wherein the endpiece is formed of a flexible material.

19. The ophthalmic surgical instrument of claim 14 wherein the fiber-optic imaging instrument includes a fiber optic cable equipped to transmit images to a monitor.

20. An ophthalmic surgical instrument for use at a surgical site, comprising:
    an endpiece configured with an inner channel there through, at least one polishing surface, a portion of the at least one polishing surface, where a portion of the polishing surface is in communication with the inner channel and configured with a plurality of recessed channels, at least a portion of the polishing surface is equipped with an abrading element extending from at least a portion of the polishing surface in a first direction, and at least one aspirating surface, where a portion of the aspirating surface is in communication with the inner channel and equipped with recessed channels; wherein a portion of the aspirating surface is configured to emulsify intraocular structures and at least a portion of the aspirating surface is configured to extend in a direction orthogonal to the first direction; and
    an inlet defined by the portion of the polishing surface and aspirating surface in communication with the inner channel and
    a fiber optic imaging instrument integral to the endpiece.

21. The ophthalmic instrument of claim 20 wherein, the endpiece is configured to illuminate the surgical site.

* * * * *